United States Patent [19]

Lekholm

[11] Patent Number: 4,763,646

[45] Date of Patent: Aug. 16, 1988

[54] HEART PACEMAKER

[75] Inventor: Anders Lekholm, Bromma, Sweden

[73] Assignee: Siemens Aktiengesellschaft, Berlin and Munich, Fed. Rep. of Germany

[21] Appl. No.: 131,269

[22] Filed: Dec. 9, 1987

Related U.S. Application Data

[63] Continuation of Ser. No. 913,269, Sep. 30, 1986, abandoned.

[30] Foreign Application Priority Data

Oct. 4, 1985 [DE] Fed. Rep. of Germany ....... 3535504

[51] Int. Cl.$^4$ .............................................. A61N 1/36
[52] U.S. Cl. .............................................. 128/419 PG
[58] Field of Search ................................... 128/419 PG

[56] References Cited

U.S. PATENT DOCUMENTS

| | | | |
|---|---|---|---|
| 2,368,207 | 1/1945 | Eaton | 128/422 |
| 3,156,235 | 11/1964 | Jaeger | 128/419 PG |
| 3,241,556 | 3/1966 | Zacouto | 128/419 PG |
| 3,358,690 | 10/1966 | Cohen | 128/419 B |
| 3,638,656 | 2/1972 | Grandjean et al. | 128/419 PG |
| 3,650,277 | 3/1972 | Sjostrand et al. | 128/419 G |
| 3,659,615 | 5/1972 | Enger | 128/419 PG |
| 3,857,399 | 12/1974 | Zacouto | 128/419 PG |
| 4,428,378 | 1/1984 | Anderson et al. | 128/419 PG |
| 4,545,380 | 10/1985 | Schroeppel | 128/419 PG |
| 4,549,548 | 10/1985 | Wittkampf et al. | 128/419 PG |
| 4,550,732 | 11/1985 | Batty, Jr. et al. | 128/419 PG |
| 4,559,946 | 12/1985 | Mower | 128/419 PG |
| 4,579,119 | 4/1986 | Callaghan | 128/419 PG |

Primary Examiner—William E. Kamm
Assistant Examiner—Timothy J. Keegan
Attorney, Agent, or Firm—Hill, Van Santen, Steadman & Simpson

[57] ABSTRACT

A heart pacemaker for supplying pacing signals to a heart includes circuitry for controlling operation of the pacemaker in dependence upon the occurrence of heart sounds. The pacemaker includes a detector for such sounds and circuitry for generating a control signal therefrom which is supplied to the basic pacing circuitry.

10 Claims, 2 Drawing Sheets

HEART PACEMAKER

This is a continuation, of application Ser. No. 913,269, filed Sept. 30, 1986 now abandoned.

BACKGROUND OF THE INVENTION

The present invention is related to heart pacemakers, and in particular to a heart pacemaker having the capability of controlling the output parameters of the stimulation pulses based on the occurrence of heart sounds.

In conventional heart pacemakers, the emitted stimulation pulses should coincide with the natural heart activity so that the pacemaker and the heart do not interfere with each other. In conventional implantable or external heart pacemakers, this is achieved by providing a detector within the pacemaker for QRS signals, P-waves or other electrical heart signals. These signals are detected and supplied via an amplifier and possibly through suitable filters to the other pacing circuitry.

SUMMARY OF THE INVENTION

It is an object of the present invention to provide a heart pacemaker having a pulse generator controlled by signals corresponding to heart activity which avoids the necessity of acquiring electrical signals from the heart for controlling the heart pacemaker.

The above object is achieved in accordance with the principles of the present invention in a heart pacemaker including a detector for cardiac sounds, which, in combination with other circuitry, generates a control signal for the basic pacing circuitry of the pacemaker. The cardiac sound detector may be a microphone, a pressure detector or an accelerometer. The detector can be disposed in a separate line leading from the pacemaker housing or in the lead connected to the electrodes for stimulating heart tissue, and can be disposed inside or outside of the pulse generator itself. P-waves, QRS complexes and other heart signals can be identified by means of suitable amplification and signal processing, which may be analog and/or digital.

From the literature (Guyton: "Textbook of Medical Physiology," Saunders, Philadelphia and London, 1966, Chapter 28 pp 399-414) it is known that the different parts of the cardiac cycle may be identified by specific sounds. For instance, the filling of the atrium or the ventricle with blood is associated with a low frequency rumbling sound while the onset of a contraction, the pumping action, is easily identified by the sharp clicking sound produced by the values as they close. On a paper recording of the heart sounds the trained eye can easily identify and separate the filling phase of the atria, contractions that pumps blood into the ventricles, the closing of the ventricular valves and the subsequent pumping action of the ventricles. The different sounds emitted at various points of the cardiac cycle differ in shape or morphology and frequency content. A band-pass amplifier with a proper response will thus easily separate the entire cardiac cycle from other sounds emitted inside or conducted through the body. With refined filtering in the frequency plane, possibly combined with circuitry for pattern recognition, it is also possible to identify the different parts of the cardiac cycle.

This possibility can be used in a dual chamber pacemaker, a so-called DDD-pacemaker that picks up the atrial signal and synchronizes or triggers the ventricular activity in accordance wit the atrial activity. Furthermore, this pacemaker inhibits its activity when a ventricular event is detected. That is, the pacemaker will not emit a stimulus that may interfere with the ventricular activity but rather resets its timing circuit so that the following stimulus will occur after a predetermined interval, normally corresponding to the preset basic rate of the pulse generator.

The differentiation between atrial activity and ventricular activity will be made easier by placing the microphone or sound transducer in the vicinity of the heart, separated from the pacemaker case in order to reduce the damping of the signals by the tissue and possibly by using two independent sound detectors placed close to the atrium and the ventricle respectively.

Since a certain variation exists in the sound patterns generated by different persons, especially in sick hearts, the detector circuit may be made programmable with respect to amplitude and frequency content of the signal and possibly also for the identification of certain patterns. The methods and circuits used for such a detector are well known from other applications and are known to those skilled in the art.

Exit blocks which are extremely difficult to measure electrically, tachycardia and fibrillations can also be detected. The detection of exit blocks is determined by the absence of heart sounds. Tachycardia is detected by monitoring the heart rate. Ventricular fibrillation is detected by monitoring selected changes in the heart sound, i.e., changes in the amplitude/frequency spectrum of the detected accoustic signals. The inefficient pumping action during fibrillation will reduce the valular activity. Thus, the sharp "clicks" associated with the closing of the values will be reduced or absent or occur at irregular intervals.

The signal generated by the detector can also be used for automatically setting the stimulation pulses, so that the stimulation threshold can be monitored at pre-programmed intervals and the stimulation pulses can be selected so as to avoid exit block. This can be accomplished by a circuit for monitoring cardiac contraction (i.e., heart sounds) at a stimultaion pulse. Such a monitoring circuit can also be employed for determining whether a stimulation pulse actually produces a cardiac contraction. If a cardiac contraction does not result following a stimulation pulse, the stimulation pulses are enlarged. The measured values may also be stored.

DESCRIPTION OF THE PREFERRED EMBODIMENTS

Figure 1:
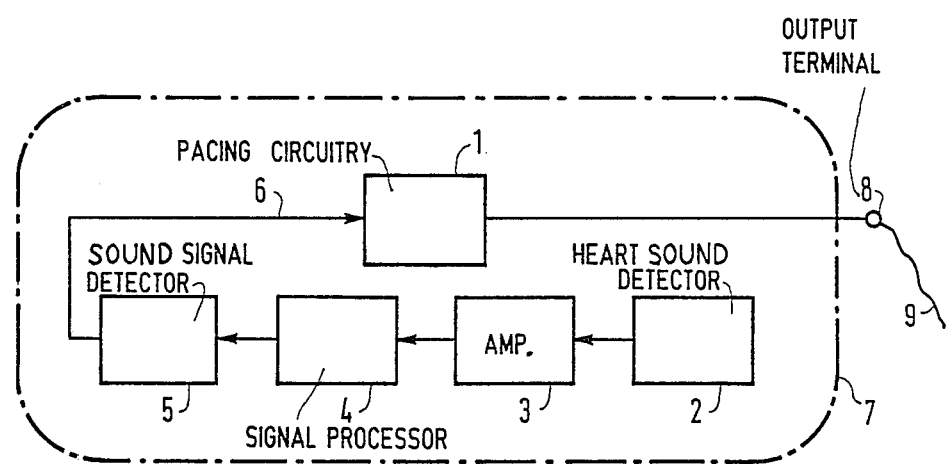
FIG. 1 is a block circuit diagram of a heart pacemaker constructed in accordance with the principles of the present invention.

A heart pacemaker is shown in FIG. 1 having pacing circuitry generally referenced at 1 for generating stimulation pulses to be supplied to heart tissue at an output terminal 8. The stimulation pulses are supplied to the heart tissue via an electrode (not shown) connected to a cable 9. The basic pacing circuitry, in addition to pulse generating circuitry, includes known circuitry for detecting cardiac contraction following a stimulation pulse, for detecting tachycardia, and for detecting fibrillation. The pacing circuitry 1 also includes circuitry for varying the duration and/or frequency of the output pulses based on detected heart events.

In accordance with the principles of the present invention, control of the pacing circuitry 1 is undertaken by a heart sound detector 2 which accoustically detects heart activity. The output of the heart sound detector 2 is supplied to an amplifier 3, which in turn supplies a signal to a signal processor for suitable shaping. The output of the signal processor 4 is supplied to a sound signal detector 5, which supplies a control signal on line 6 to the pacing circuitry 1. Since the heart sound detector 2 detects all types of heart activity in an essentially non-discriminatory manner, the sound signal detector 5 is employed to selectively supply a control signal, if desired, only under given conditions, or to vary a continuously supply control signal only under given conditions.

All of the components can be accomodated within a housing 7 of the pacemaker.

The heart sound detector 2 may be any type of detector suitable for accoustically monitoring heart activity. The detector 2, may, for example, be a microphone, a pressure detector, or an accelerometer. The detector 2 can be disposed within the housing 7, in a separate line external to the housing 7, or in the same cable 9 to which the stimulation electrode or electrodes are attached.

In addition to the functions described, the pacing circuitry 1 may include circuitry for preventing exit block.

Figure 2:
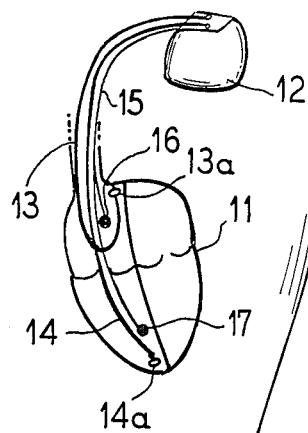
FIG. 2 is a schematic showing of the arrangement of sensors with respect to a heart for a pacemaker constructed in accordance with the principles of the present invention in a first embodiment.

FIG. 2 depicts an embodiment of the detector based on pressure, in this case intracardiac pressure variations.

In FIG. 2, a separate lead 15 is used for the detection of cardiac pressures. This lead 15 is placed inside the heart 11 in the same manner as the normal pacemaker leads, such as an atrial lead 13 having an electrode 13a and a ventricular lead 14 having a ventricular electrode 14a. In this case, the lead 15 is used to detect intracardiac pressures in the atrium and in the ventricle. This is achieved by placing two small pressure transducers 16 and 17 respectively at sites that coincide with the atrium and the ventricle.

An alternative design has the pressure transducers mounted inside the pacemaker can 12. The sensing of the intra-atrial and intraventricular pressure is then achieved by the connection of a catheter from the transducers in the pacemaker can 12 to the heart 11. The catheter has two tubes or lumens that are typically filled with a fluid that is an efficient transmitter of pressures from inside the heart to the pressure transducers. The two lumens are sealed with a thin membrane at the points inside the heart where pressure is to be measured.

The pressure catheter or catheters may also be incorporated in and made as part of the pacemaker lead, which, in addition to the normal conducting wires etc., contains additional wires to the pressure transducer or an additional lumen for the transmission of pressures to the transducer or transducers placed inside the pacemaker pulse generator can.

Figure 3:
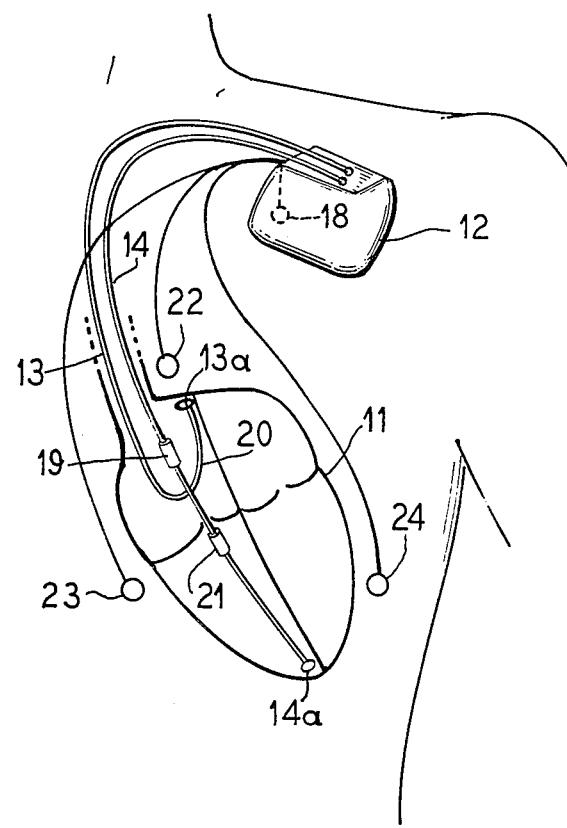
FIG. 3 is a schematic showing of the arrangement of sensors with respect to a heart for a pacemaker constructed in accordance with the principles of the present invention in a second embodiment.

FIG. 3 depicts several embodiments and placements of a microphone or accelerometer for the detection of cardiac sounds. As seen in the drawing, the microphones or accelerometers 22, 23 and 24 may be placed either in close proximity to the atrium or the ventricle or at a position where sounds from the atria and ventricles are equally well transmitted to the transducer. A pressure transducer 18 can be placed inside the pacemaker can 12 is depicted. One of several such transducers may be used simultaneously, depending on the application and the function of the system.

Pressure transducers 19, 20 and 21 may be placed approximately at the indicated positions in the pacemaker lead, or orifices connected to a lumen can instead be placed at those locations which transmit the pressure variations to pressure transducer placed inside the pacemaker can 12. In a different embodiment these three transducers may be sensitive to sound or acceleration.

Although modifications and changes may be suggested by those skilled in the art it is the intention of the inventor to embody within the patent warranted hereon all changes and modifications as reasonably and properly come within the scope of his contribution to the art.

I claim as my invention:

1. A heart pacemaker comprising:
   a housing having a size adapted for implantation in a patient;
   pulse generator means in said housing for generating pulses for supply to heart tissue of said patient;
   acoustic detector means disposed relative to said heart for detecting heart sounds and for generating electrical signals corresponding thereto, said acoustic detector means having a size adapted for implantation in said patient with said housing; and
   means in said housing connected to said acoustic detector means and to said pulse generator means for controlling said pulse generator based on said electrical signals.

2. The pacemaker of claim 1, wherein said detector means is a microphone.

3. The pacemaker of claim 1, wherein said detector means is a pressure detector.

4. The pacemaker of claim 1, wherein said detector means is an accelerometer.

5. The pacemaker of claim 1, wherein said pacemaker has an electrode lead attached to the heart tissue for supplying said pulses thereto, and wherein said detector means is disposed in said electrode lead.

6. The pacemaker of claim 1, wherein said detector means is disposed inside said housing.

7. The pacemaker of claim 1, wherein said detector means is disposed outside of said housing.

8. The pacemaker of claim 1, wherein said pulse generator means includes means for monitoring cardiac contraction following emission of a stimulation pulse, said means for monitoring cardiac contraction being connected to said detector means.

9. The pacemaker of claim 1, wherein said pulse generator means includes means for monitoring for tachycardia, said means for monitoring for tachycardia being connected to said detector means.

10. The pacemaker of claim 1, wherein said pulse generator means includes means for monitoring for heart fibrillation, said means for monitoring for heart fibrillation being connected to said detector means.

* * * * *